(12) United States Patent
Ozdil et al.

(10) Patent No.: US 9,877,727 B2
(45) Date of Patent: Jan. 30, 2018

(54) DIVERTICULUM TREATING DEVICE

(71) Applicant: Empire Technology Development LLC, Wilmington, DE (US)

(72) Inventors: Deniz Ozdil, New South Wales (AU); Phillip Marathakis, New South Wales (AU); Gregory James Roger, New South Wales (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 582 days.

(21) Appl. No.: 14/001,764

(22) PCT Filed: May 2, 2013

(86) PCT No.: PCT/US2013/039218
§ 371 (c)(1),
(2) Date: Aug. 27, 2013

(87) PCT Pub. No.: WO2014/178869
PCT Pub. Date: Nov. 6, 2014

(65) Prior Publication Data
US 2015/0112129 A1    Apr. 23, 2015

(51) Int. Cl.
*A61B 1/018*    (2006.01)
*A61B 1/06*    (2006.01)
(Continued)

(52) U.S. Cl.
CPC ........ *A61B 17/12145* (2013.01); *A61B 1/018* (2013.01); *A61B 1/06* (2013.01);
(Continued)

(58) Field of Classification Search
CPC .......... A61B 17/0057; A61B 17/12022; A61B 17/12099; A61B 17/12104;
(Continued)

(56) References Cited

U.S. PATENT DOCUMENTS

| 5,100,419 A | 3/1992 | Ehlers |
| 6,241,747 B1 | 6/2001 | Ruff |

(Continued)

FOREIGN PATENT DOCUMENTS

| RU | 2 404 717 | 11/2010 |
| WO | WO 2007/017562 | 2/2007 |
| WO | WO 2011/140400 | 11/2011 |

OTHER PUBLICATIONS

Kothari, T. H. et al., "The over-the-scope clip system—a novel technique for gastrocutaneous fistula closure: The first North American experience," *Can J Gastroenterol*, vol. 26, No. 4, pp. 193-195 (Apr. 2012).

(Continued)

*Primary Examiner* — Eric Rosen
*Assistant Examiner* — Mikail Mannan
(74) *Attorney, Agent, or Firm* — Maschoff Brennan

(57) ABSTRACT

A system for treating a diverticulum in a body lumen includes a tubular member including a lumen and an elongate member in an elongated state within the lumen of the tubular member. The elongate member is configured to form a coiled state when removed from the tubular member.

14 Claims, 8 Drawing Sheets

(51) Int. Cl.
*A61B 17/00* (2006.01)
*A61B 17/12* (2006.01)
*A61B 1/31* (2006.01)
*A61B 17/064* (2006.01)

(52) U.S. Cl.
CPC ............ *A61B 1/31* (2013.01); *A61B 17/0057* (2013.01); *A61B 17/1214* (2013.01); *A61B 17/12031* (2013.01); *A61B 17/12099* (2013.01); *A61B 17/12113* (2013.01); *A61B 2017/00278* (2013.01); *A61B 2017/00296* (2013.01); *A61B 2017/00566* (2013.01); *A61B 2017/00575* (2013.01); *A61B 2017/00592* (2013.01); *A61B 2017/00623* (2013.01); *A61B 2017/00632* (2013.01); *A61B 2017/00668* (2013.01); *A61B 2017/00818* (2013.01); *A61B 2017/00867* (2013.01); *A61B 2017/0649* (2013.01); *A61B 2017/1205* (2013.01)

(58) Field of Classification Search
CPC ........ A61B 17/12109; A61B 17/12122; A61B 17/1214; A61B 17/12168; A61B 2017/00575; A61B 2017/00592; A61B 2017/0061; A61B 2017/00623; A61B 2017/00641; A61B 2017/00646; A61B 2017/00659; A61B 2017/00668; A61B 2017/06171; A61L 317/061661

USPC ............... 606/151, 153, 213, 215, 216, 219; 600/104; 623/23.64, 23.65, 23.69, 23.7, 623/23.71
See application file for complete search history.

(56) References Cited

U.S. PATENT DOCUMENTS

| | | | |
|---|---|---|---|
| 6,663,633 B1 * | 12/2003 | Pierson, III | A61B 17/0469 606/148 |
| 7,842,054 B2 | 11/2010 | Green, Jr. et al. | |
| 8,007,427 B2 | 8/2011 | Reed et al. | |
| 8,357,193 B2 | 1/2013 | Phan et al. | |
| 8,721,664 B2 | 5/2014 | Ruff et al. | |
| 2007/0243225 A1 * | 10/2007 | McKay | A61K 9/0024 424/423 |
| 2010/0280313 A1 * | 11/2010 | Gasche | A61B 1/00135 600/104 |
| 2012/0065582 A1 | 3/2012 | Noda et al. | |
| 2012/0089157 A1 * | 4/2012 | Forsell | A61F 5/0036 606/139 |

OTHER PUBLICATIONS

International Search Report and Written Opinion in PCT/US2013/039218, dated Jul. 19, 2013.

* cited by examiner

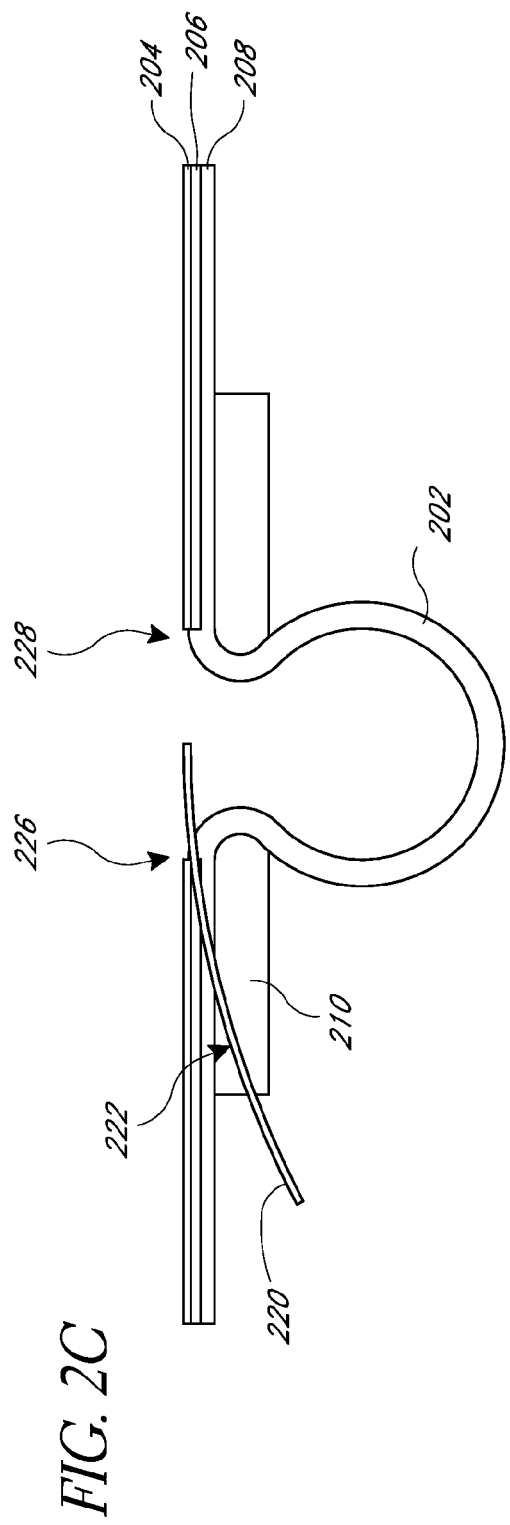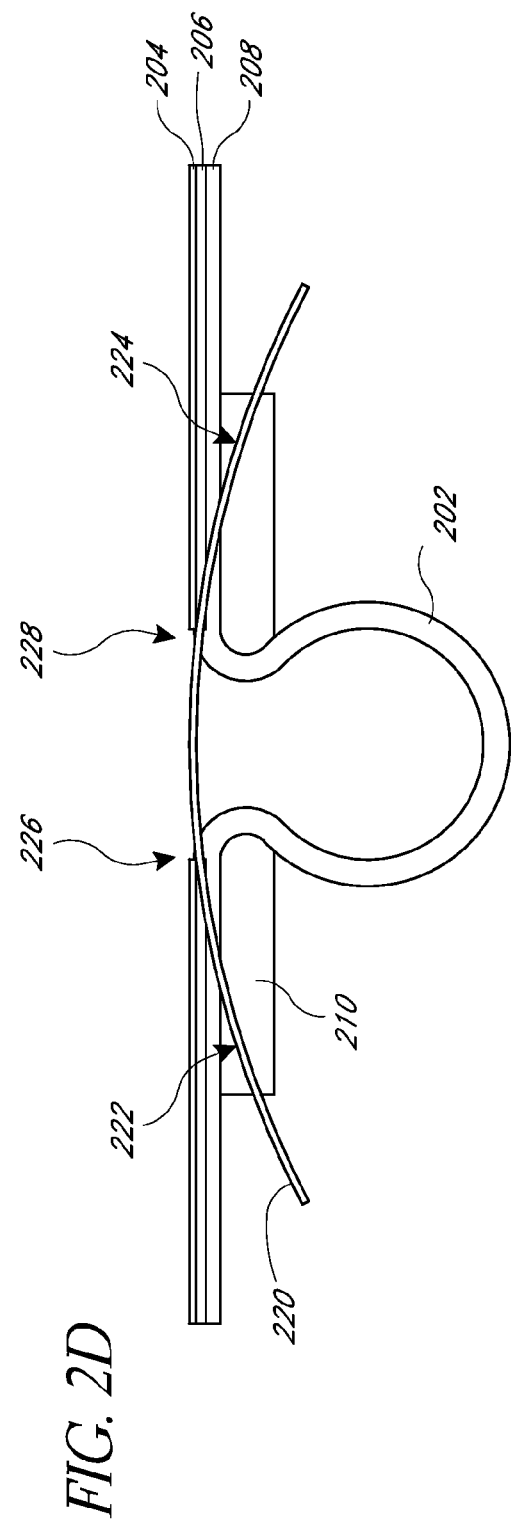

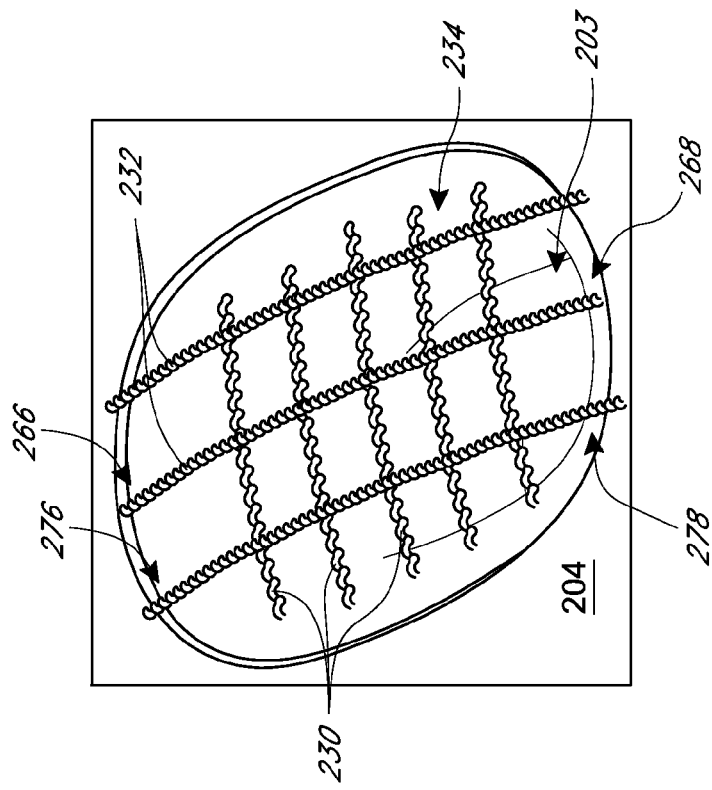
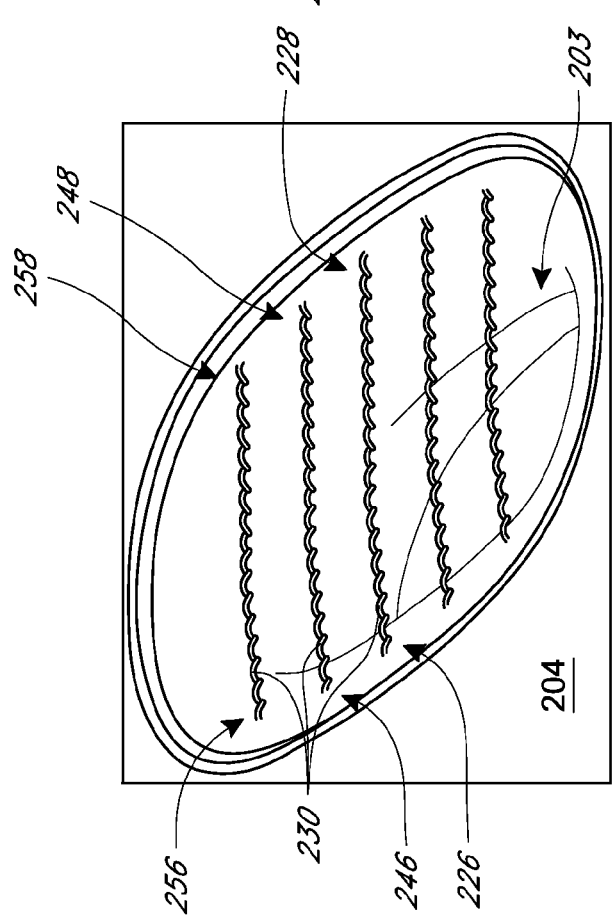
*FIG. 2I*
*FIG. 2H*

DIVERTICULUM TREATING DEVICE

CROSS-REFERENCE TO RELATED APPLICATIONS

This application is a United States national stage application under 35 U.S.C. §371 of PCT Application No. PCT/US2013/039218 designating the United States, filed on May 2, 2013, the contents of which are incorporated herein by reference in their entirety.

BACKGROUND

An outpouching of the colon or other body lumen, called a diverticulum, can become the site for inflammation known as diverticulitis, microperforation, infection, and/or bleeding. Current treatments may involve the surgical removal of segments of the body lumen. For extreme cases of diverticulitis, treatment can involve colon resection and placement of a colostomy. These approaches can result in significant healthcare costs and substantial pain for patients.

SUMMARY

A system for treating a diverticulum can include an elongate member or plurality of elongate members that can seal an inverted diverticulum and provide a structure for targeted healing across the smooth muscle wall surrounding the diverticulum. The elongate member is elongated in a first or delivery state and contracted in a second or deployed state. The elongate member can be advanced and positioned within the lumen of a tubular member such as a pre-curved needle, for example through a working channel of a colonoscope. Upon deployment, the elongate member can radially expand and/or longitudinally contract. The elongate member may pierce through tissue in opposite sides of the neck of an outpouched or inverted diverticulum and pull the opposite sides of the neck of the outpouched or inverted diverticulum toward each other or together. The elongate member can include a coiled spring shape such that the first shape is a stretched out coil and the second shape is a coil configured to draw opposite sides of the neck of the inverted diverticulum toward each other. A plurality of elongate members can improve closure and stimulate healing.

In some implementations, a method for treating a diverticulum in a body lumen includes disposing an elongate member in a coiled state through a first region of a muscular layer of the body lumen and through a second region of the muscular layer of the body lumen. The diverticulum may be inverted and between the first region and the second region. Disposing the elongate member may include inserting a tubular member through the first region of the muscular layer and through the second region of the muscular layer, and removing the elongate member from the lumen of the tubular member. During inserting the tubular member, the elongate member may be in an extended state in a lumen of the tubular member. The method may further include disposing a collar around a mouth of an inverted diverticulum or a tissue scaffold plug within the lumen of an outpouched diverticulum. The elongate member in the coiled state may include a coiled portion and one or more spacer elements between windings of the coiled portion, wherein the spacer elements are longitudinally compressible by the coiled portions. The method may further include disposing a second elongate member in a coiled state through a third region of the muscular layer of the body lumen and through a fourth region of the muscular layer of the body lumen. The inverted diverticulum may be between the third region and the fourth region. After disposing the elongate member and disposing the second elongate member, a longitudinal axis of the elongate member and a longitudinal axis of the second elongate member may form an angle that is less than about 10°. After disposing the elongate member and disposing the second elongate member, a longitudinal axis of the elongate member and a longitudinal axis of the second elongate member may form an angle that is between about 80° and about 100°. Disposing the second elongate member may include inserting a second tubular member through the third region of the muscular layer and through the fourth region of the muscular layer, and removing the second elongate member from the lumen of the second tubular member. During inserting the second tubular member, the second elongate member may be in an extended state in a lumen of the second tubular member. The method may further include disposing a plurality of elongate members through regions of the muscular layer of the body lumen on opposite sides of the inverted diverticulum. The plurality of elongate members may include a first plurality of elongate members substantially parallel to each other and a second plurality of elongate members substantially parallel to each other and substantially transverse to the first plurality of elongate members. The method may further include, prior to disposing the elongate member, inverting the diverticulum. The body lumen may include an intestine. In some implementations, the elongate member is not a guide wire.

In some implementations, a system for treating a diverticulum in a body lumen includes a tubular member including a lumen and an elongate member in an elongated state within the lumen of the tubular member. The elongate member is configured to form a coiled state when removed from the tubular member.

The system may further include a pusher configured to maintain a longitudinal position of the elongate member upon retraction of the tubular member. The elongate member may be bioabsorbable. The elongate member may include a polymer. The polymer may include at least one of polylactic acid (PLA), poly(lactic-co-glycolic acid) (PLGA), polyglycolic acid (PGA), poly-L-lactic acid (PLLA), poly-D-lactic acid (PDLA), poly-D,L-lactic acid (PDLLA), poly(L-lactic-co-D,L-lactic acid) (PLDLLA), poly(L-lactide-co-L-lysine), poly(4-hydroxy-L-proline ester), poly[α-(4-aminobutyl)-L-glycolic acid], polycaprolactone (PCL), poly(ortho esterpoly (caprolactone)), polyhydroxybutyrate (PHB), polyethylene imine, polyanhydrides, polyhydroxyalkanoate (PHA), polyethylene terephthalate (PET), naturally derived bioabsorbable polymers (NDB), and copolymers thereof. The elongate member in the coiled state may have a length of less than about 5 cm. The elongate member in the coiled state may have a radius of less than about 1 mm. The elongate member in the coiled state may have a pitch of less than about 1 mm. The elongate member may include a textured surface. The elongate member may include a coiled portion and one or more spacer elements between windings of the coiled portion. The spacer elements may be longitudinally compressible by the coiled portions. The coiled portion may be bioabsorbable. The spacer elements may be bioabsorbable. The spacer elements may be configured to have a rate of bioabsorbtion that is greater than a rate of bioabsorbtion for the coiled portion. In some implementations, the elongate member is not a guide wire. An assembly for treating a diverticulum in a body lumen can include a catheter including a working channel and the system at least partially within the working channel. A colonoscope may include the catheter. The colonoscope may further include a light source and a viewing lens. An assembly for treating a diverticulum in a body lumen can include a catheter including a working channel and a plurality of the systems at least partially within the working channel. A colonoscope may include the catheter. The colonoscope may further include a light source and a viewing lens.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

FIGS. 2A-2I schematically illustrate an example method of treating a diverticulum of the sigmoid colon.

DETAILED DESCRIPTION

Figure 1B:
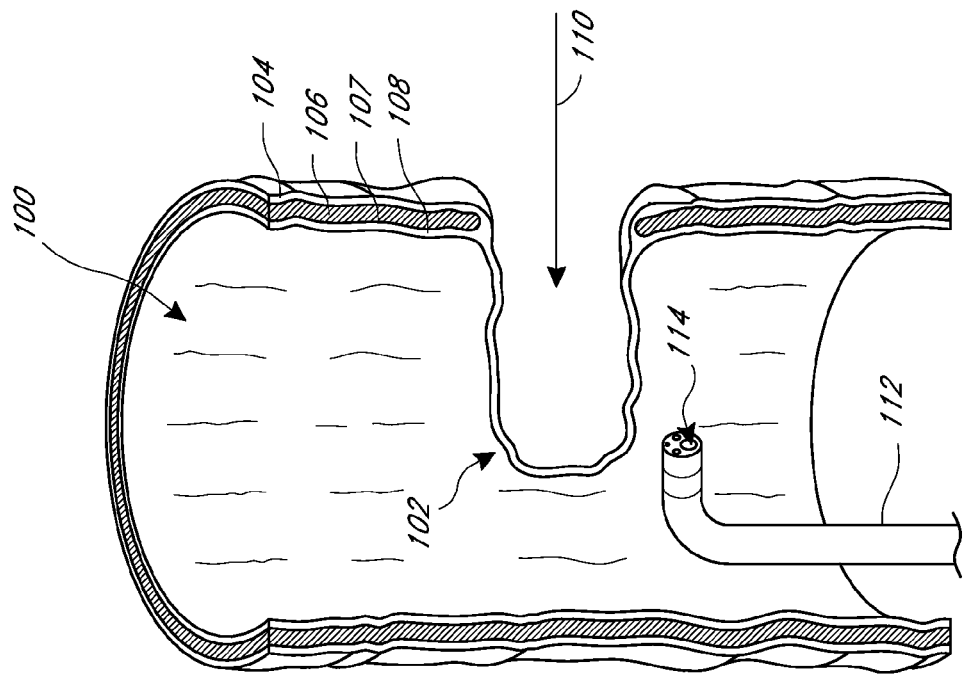
FIG. 1B is a cross-sectional view of an inverted diverticulum of the sigmoid colon.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Described herein are various components of the device or apparatus which may be made of a shape memory alloy (SMA). The use of a SMA in medical devices is well known in the art and those skilled in the manufacture and use of medical devices having component(s) made from SMA will appreciate its utility in the descriptions herein. In addition to SMA, any component of any embodiment described herein may be made from any medical grade material, including but not exclusively limited to any metal, alloy, polymer, fiber, ceramic, or any combinations thereof.

Diverticula of the intestine such as the lower colon can become the site for microperforation and inflammation called diverticulitis and/or bleeding. A device disclosed herein can be used to close inverted diverticula of the colon, sparing the patient of colon resection surgery. Current treatment strategies for treating diverticula may involve the surgical removal of large segments of the colon, and in extreme cases, the placement of a colostomy. An alternative treatment strategy is provided that can be performed during routine colon examinations, where a colonoscope is used to identify a diverticulum, and can also deliver the tools to the site for ligating the diverticulum. The working channel of the colonoscope or other catheter may be used to deliver one or a series of elongate coils, which snares and ties off the inverted diverticulum. The device may be configured to fit within the working channel of the colonoscope, thereby allowing the physician/operator to identify an individual diverticulum and tie it off with a ligation at the base of the diverticulum. Means can be provided to verify that the full diverticulum is inverted and that the base is sealed in such a manner as to reduce the opening in the muscular layer of the colon wall, to reduce or minimize circulation of blood into the tissue.

In conventional colonoscopy procedures, a gastroenterologist advances a colonoscope completely to the patient's appendix while inflating the colon with air. Visual examination is preformed while retracting the colonoscope. Diverticula are generally easy to see and diagnose visually. If treatment of the diverticulum is deemed warranted by the physician, the whole colonoscope must be removed (4-5 ft. long) in order to slide an overtube assembly onto the colonoscope. Then the colonoscope is reinserted while looking to find the diverticulum. This is a tedious, time-consuming, and potentially dangerous procedure. In contrast, according to embodiments disclosed herein, once a diverticulum is detected, the physician can keep the colonoscope in the colon and focused on the diverticulum, and advance the disclosed device down the working channel of the colonoscope in order to treat the diverticulum quickly. Once the diverticulum is inverted and tied off, further examination of the colon can continue and other treatments, such as polyp removal, can continue also using the working channel. The substantial burden of removing the colonoscope from the patient, sliding an overtube assembly onto the distal end of the colonoscope, reinserting the colonoscope with overtube assembly, and relocating the diverticulum is completely gone.

Disclosed herein are tools, devices, assemblies, and methods for closing diverticula in a body lumen. The tools, devices, and assemblies may be configured for endoscopic delivery through a lumen of a catheter, e.g., through a working channel of a colonoscope.

Figure 1A:
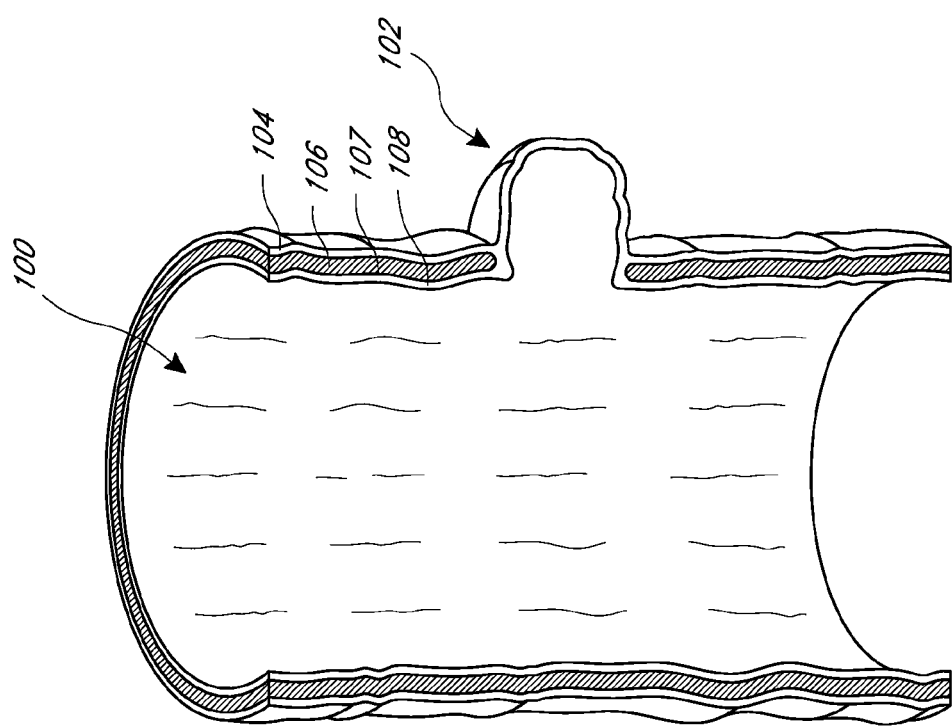
FIG. 1A is a cross-sectional view of a diverticulum of the sigmoid colon.

FIG. 1A is a cross-sectional view of a diverticulum 102 of a sigmoid colon 100. The walls of the colon 100 generally include an outer layer of serosa 104, an inner layer of mucosa 108, and a muscular layer 106, or muscularis, between the mucosa 108 and the serosa 104. In the region of a typical diverticulum 102, a hole may exist in the muscular layer 106, in which case the walls of the diverticulum 102 may have only the outer layer of serosa 104 and the inner layer of mucosa 108. A submucosal region 107 also exists between the mucosa 108 and serosa 104 layers. A diverticulum 102 typically bulges one to two centimeters through the wall of the colon 100. The devices and methods described herein can be used to treat diverticula 102 in other portions of the intestine, as well.

FIG. 1B is a cross-sectional view of the diverticulum 102 of the sigmoid colon 100 after the diverticulum 102 has been at least partially inverted into the lumen of the colon 100. A negative pressure may be applied through a catheter such as a working channel of a colonoscope, for example proximate to a specific diverticulum 102, thereby causing the diverticulum 102 to at least partially invert into the body lumen. The negative pressure may be applied non-specifically within the body lumen itself, thereby causing any or at least some diverticula 102 to at least partially invert into the body lumen. Either with or instead of a negative pressure, a positive pressure may be applied from outside the body lumen. For example, a positive pressure may be applied to the body cavity within which the body lumen resides (e.g., to the peritoneal cavity, thereby causing any or some diverticula 102 to at least partially invert into the colon 102). Alternatively, a positive pressure may be applied via a laparoscopic tube directly to a specific diverticulum 102, causing the diverticulum 102 to at least partially invert into the colon 102. Inversion of the diverticulum 102 between the state illustrated in FIG. 1A and the state illustrated in FIG. 1B is shown by the arrow 110. After inversion, the tissue of the diverticulum 102 is within the lumen of the colon 100. The devices and procedures described below generally refer to diverticula 102 after inversion.

During inversion of the diverticulum 102, fecaloma or the like that were entrapped in the diverticulum 102 may be pushed out into the lumen of the colon 100. Such entrapped material can cause rupture of the diverticulum 102, which can lead to further serious complications such as bleeding and/or infection of the tissue of the peritoneal cavity. Even absent further treatment of the inverted diverticulum 102 as described below, inversion of the diverticulum 102 may itself be beneficial.

FIG. 1B also illustrates an example colonoscope 112 including a working channel or lumen 114. Tools such as biopsy forceps, graspers, and manipulators, as well as devices such as the tubular member 220 described below may be passed through the working channel 114. The colonoscope 112 can also include one or more of a light source useful to illuminate a viewing area, a viewing lens, a lumen for delivering fluid such as saline, air, negative pressure, etc.

Figure 2A:
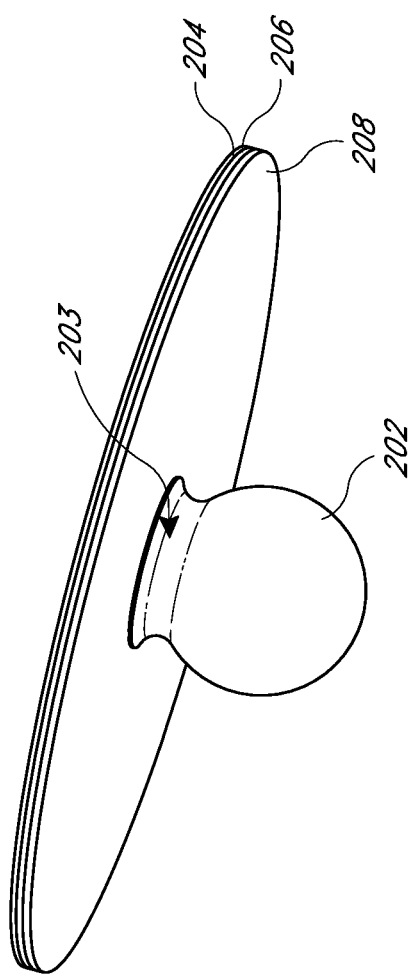

FIGS. 2A-2I schematically illustrate an example method of treating a diverticulum 202 of the sigmoid colon. FIG. 2A is a bottom perspective view of an diverticulum 202 after the diverticulum 202 has been at least partially inverted, for example as described above with respect to FIG. 1B. The walls of the colon include an outer layer of serosa 204, an inner layer of mucosa 208, and a muscular layer 206 between the mucosa 208 and the serosa 204. The diverticulum 202 has a base or neck or mouth 203 where the mucosa 208 diverges from the wall of the colon. An inverted diverticulum 202 may resemble a uvula.

Figure 2B:
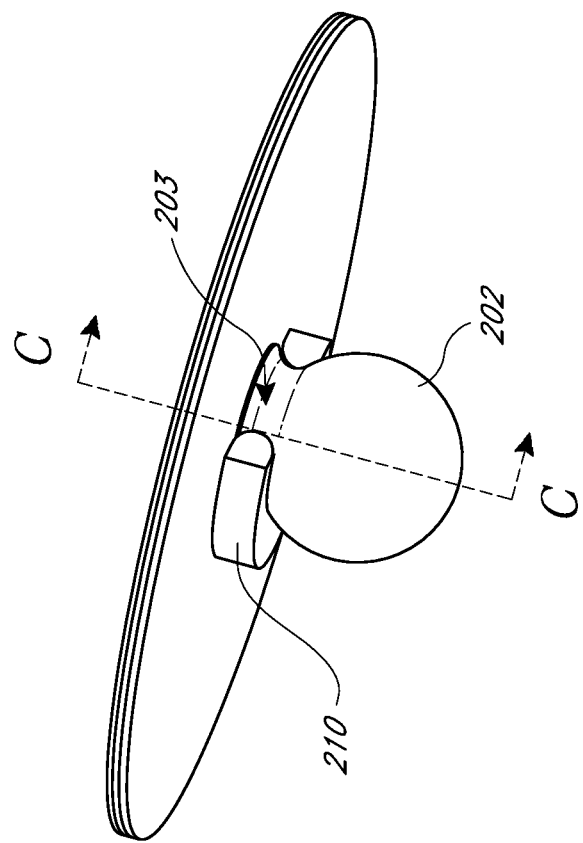

FIG. 2B is a bottom perspective view of the inverted diverticulum 202 after a colonoscopic targeting device or collar 210 has been placed around the base 203 of the diverticulum 202. The device 210 may help to maintain the diverticulum 202 in an inverted state, for example during fluctuations in applied inversion pressure or allowing discontinuation of the application of inversion pressure. The device 210 has a general C-shape that allows it to be placed around the base 203 of the diverticulum 202. Portions or arms of the device 210 may provide a target for later treatment steps. For example, the device 210 may include a series of apertures configured to guide deployment lumens through certain parts of the base 203 of the diverticulum 202.

FIG. 2C is a cross-sectional view of the diverticulum 202 along the line C-C of FIG. 2B. A deployment catheter or tubular member 220 has been disposed through a first region 226 of the mucosal layer 206 of the body lumen. For example, the catheter 220 can be advanced through the working channel of a colonoscope, which can allow the method to be performed during a routine colonoscopy. A system including the catheter 220 and an elongate member 230 therein (as described below), and optionally the device 210, may be classified as a Class IIb medical device that is easy to implement, for example because adjuncts or changes to surgical procedures may not be needed.

The catheter 220 may be inserted into a first lumen 222 of the device 210, which can help to properly position or orient the deployment catheter 220 with respect to the first region. Alternatively, the catheter 220 can pierce the device 210. The catheter 220 may include, for example, a hollow, pre-curved needle. After traversing through the first region 226, the catheter 220 continues towards a second region 228 of the muscular layer 206. The inverted diverticulum 202 is between the first region 226 and the second region 228. FIG. 2D shows the diverticulum 202 after the catheter 220 is disposed through the second region 228 of the muscular layer 206 of the body lumen on the second side 228 of the inverted diverticulum 202. In FIG. 2D, the tubular member 220 penetrates the mucosal layer 208 in the first region 226, curves up into the smooth muscle layer 206 in the first region 226, across the mouth 203, curves down into the smooth muscle layer 206 in the second region 228, and penetrates out of the mucosal layer 208 in the second region 228 and into the lumen or cavity of the colon.

Figure 2E:
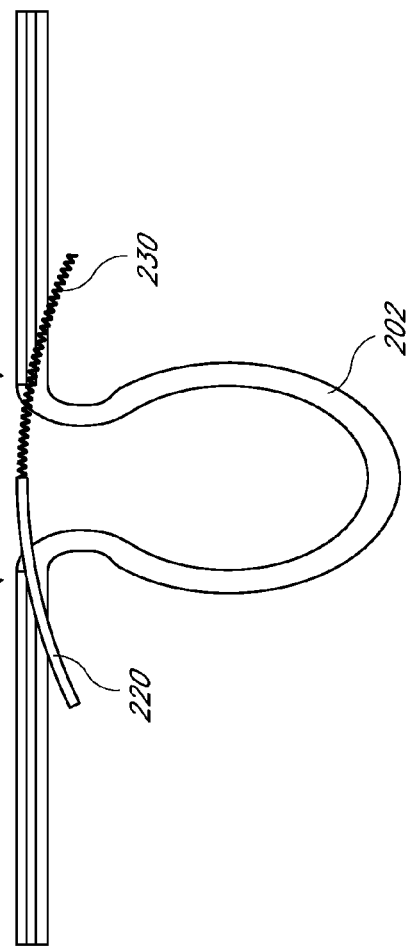
Figure 2F:
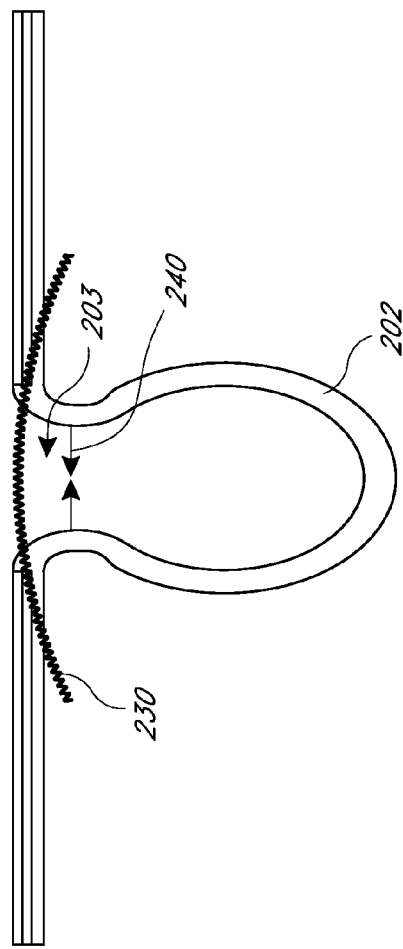

FIG. 2E shows the diverticulum 202 after the catheter 220 is retracted from the second region 228 of the muscular layer 206, which can remove an elongate member or dart or tie 230 from a lumen of the catheter 220, for example by maintaining the position of the elongate member 230 using a pusher or plunger in the lumen of the catheter 220. A system can include the catheter 220 (e.g., including the pusher) and the elongate member 230. An assembly can include a deployment catheter including working channel and the system including the catheter 220 and the elongate member 230 at least partially within the working channel. An assembly can include a deployment catheter including working channel and a plurality of systems each including a catheter 220 and an elongate member 230 at least partially within the working channel. The deployment catheter may be, for example, a working channel of a colonoscope. As described above, the colonoscope may include a light and a viewing lens. In some implementations, the elongate member 230 is not a guide wire.

Figure 3:
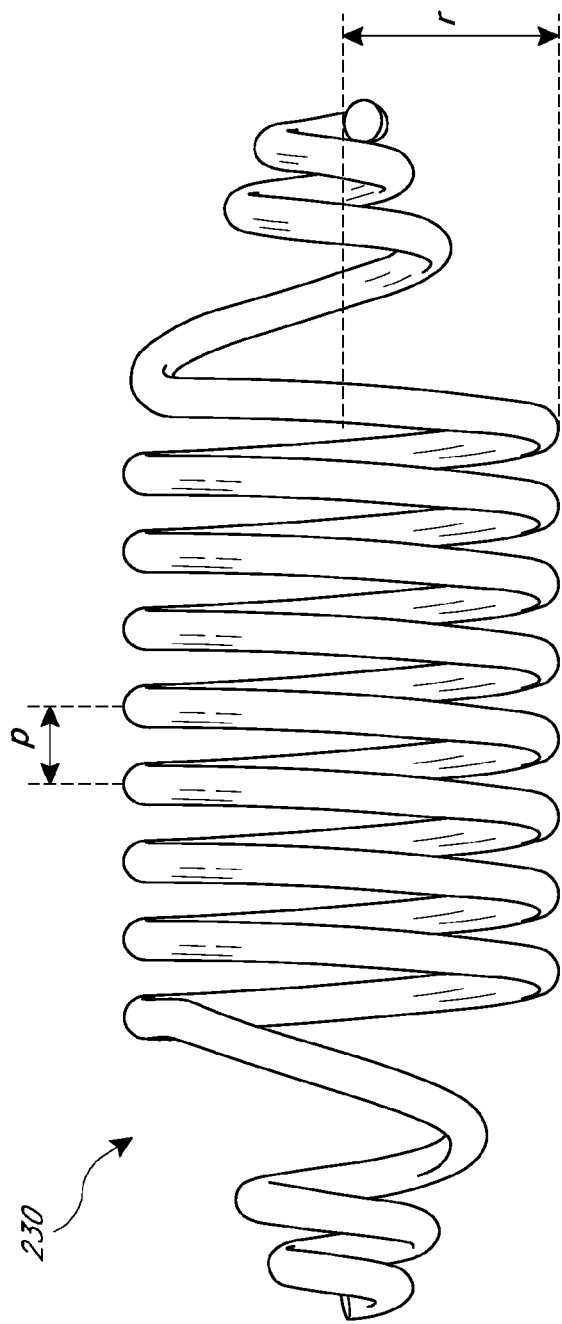
FIG. 3 is a side elevational view of an example elongate member.

FIG. 3 is a side elevational view of an example elongate member 230. The elongate member 230 has a constrained shape or state when confined within the lumen of the catheter 220 and an expanded shape or state when released or removed from the lumen of the catheter 220. The expanded shape may be coiled (e.g., a coiled shape, as illustrated in FIG. 3) and the constrained shape may be substantially straight or similar to a stretched or flattened coil. The expansion of the expanded shape may refer to radial expansion of the elongate member 230, for example because the elongate member 230 may longitudinally contract or foreshorten in the expanded shape compared to the constrained shape. The elongate member 230 may self-expand from the constrained shape to the expanded shape when not retrained.

For example, referring again to FIG. 2E, as the catheter 220 is proximally retracted, the elongate member 230 remains in place (e.g., due to a pusher or plunger acting on a proximal end of the elongate member 230) and expands radially outward. This outward radial expansion can help to anchor the elongate member 230 in the tissue proximate to the inverted diverticulum 202. The outward radial expansion can include a twisting component, which can help to screw the end of the elongate member 230 into the tissue proximate to the inverted diverticulum 202, which can provide stronger anchoring. However, absence of sharp parts can reduce or avoid irritation of the tissue.

The coiled structure of the elongate member 230 can allow for longitudinal movement, allowing for normal colon motility during peristalsis. This movement can inhibit the area treated by an elongate member 230 from being compromised, for example tearing the elongate member 230 out of the tissue.

In the expanded shape, the elongate member 230 may have a length of less than about 5 cm, less than about 3 cm, or less than about 1 cm. In the expanded shape, the elongate member 230 may have a radius r of less than about 2 mm, less than about 1 mm, or less than about 0.5 mm. The radius r of the elongate member 230 may vary across the length of the elongate member 230. In the expanded shape, the elongate member 230 may have a pitch or distance between windings p of the coil of less than about 10 mm, less than about 5 mm, or less than about 1 mm, including about 0 mm (e.g., the windings in contact with each other). The pitch p of the elongate member 230 may vary across the length of the elongate member 230.

The elongate member 230 may include a bioabsorbable material. The elongate member 230 may include a polymer (e.g., a biodegradable or resorbable polymer). For example, the elongate member may include at least one of polylactic acid (PLA), poly(lactic-co-glycolic acid) (PLGA), polyglycolic acid (PGA), poly-L-lactic acid (PLLA), poly-D-lactic acid (PDLA), poly-D,L-lactic acid (PDLLA), poly(L-lactic-co-D,L-lactic acid) (PLDLLA), poly(L-lactide-co-L-lysine), poly(4-hydroxy-L-proline ester), poly[α-(4-aminobutyl)-L-glycolic acid], polycaprolactone (PCL), poly(ortho esterpoly (caprolactone)), polyhydroxybutyrate (PHB), polyethylene imine, polyanhydrides, polyhydroxyalkanoate (PHA), polyethylene terephthalate (PET), naturally derived bioabsorbable polymers (NDB), copolymers thereof, and the like.

The elongate member 230 or parts thereof (e.g., ends) may include a textured or roughened surface. The surface may be roughened, for example, by chemical (e.g., acid) etching, sand blasting, grit blasting, grinding, abrading, combinations thereof, and the like. The surface may be roughened during casting of rods that are bent and/or trained to be coiled. The surface may be roughened by adding granular and rough coatings, which during resorption can have the roughened surface eroded. The roughening may be directionally aligned, such as barbs, to enhance the grip on the surrounding soft tissue in sympathy with the desire to draw opposite ends towards each other. A roughened surface can provide more surface area to help the elongate member 230 grip tissues proximate to the mouth 203 of the diverticulum 202. A roughened surface may be useful for attaching spacer elements (described below) and/or for attaching drugs or drug coatings. The drug or drug coating may include antibiotics to inhibit or prevent infection while the injured tissue is healing and/or coagulation modifiers to reduce or minimize blood loss and promote rapid healing. Examples of antibiotic drugs that may be used include amoxicillin-clavulanate (augmentin), trimethoprim-sulfamethoxazole (co-trimoxazole), fluoroquinolone, metronidazole (flagyl), clindamycin (cleocin), aminoglycoside, gentamicin, tobramycin, monobactam (aztreonam), cephalosporin, ceftriaxone, ceftazidime (fortaz), cefotaxime, cefoxitin (mefoxin), cefotetan, an β-lactamase inhibitors (e.g., ampicillin-sulbactam, ticarcillin-clavulanate (timentin)). Other antibiotics are also possible. Examples of coagulation modifiers that may be used include oxidized cellulose, absorbable gelatin, fibrin foam, thrombin, and microfibrillar collagen. Other coagulation modifiers are also possible. A coating that includes tissue activation factors to promote local cell growth may be included. An absorbent coating may be applied, to which may be added any liquid of choice (e.g., an antibiotic liquid) at the time of a procedure. An absorbent coating can allow the nature of one or more compounds eluted from the coating to be customized by a user of the device proximate to or during a procedure.

Figure 4:
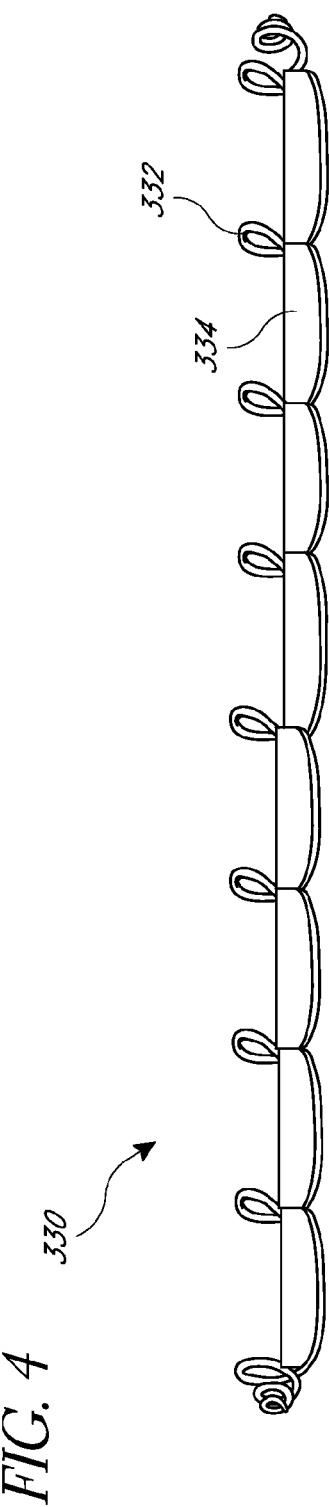
FIG. 4 is a side elevational view of another example elongate member.

FIG. 4 is a side elevational view of another example elongate member 330. The elongate member 330 includes a support structure or coiled portion 332 and a plurality of spacer elements 334. The support structure 332 may be similar to the elongate member 230, for example including the same material, shapes, features, dimensions, combinations thereof, and the like. The spacer elements 334 are between windings of the coiled portion 332, and are longitudinally compressible by the coiled portion 332. The spacer elements 334 may be absent from the ends of the elongate member 330, which can allow the ends of the elongate member 330 to retract into a shape that anchors the elongate member 330 in the tissue at the mouth of an inverted diverticulum. The spacer elements 334 can account for initial swelling across the mouth of the inverted diverticulum. As swelling reduces, healing begins and the spacer elements 334 are absorbed, allowing contraction of the coiled portion 332, which can allow contraction of to follow the natural progression of healing. Upon degradation of the spacer elements 334, complete recoil of the coiled portion 332 can occur.

The elongate member 330 may be absent of barbs or the like because the ends of the coiled portion 332 are designed to anchor the elongate member 330 in tissue around an inverted diverticulum. For example, the absence of sharp parts can inhibit or avoid irritation of the tissue. However, barbs are also possible, for example for increased anchoring properties.

The coiled portion 332 may include a polymer (e.g., a biodegradable or resorbable polymer). For example, the coiled portion 332 may include at least one of PLA, PLGA, PGA, PLLA, PDLA, PDLLA, PLDLLA, poly(L-lactide-co-L-lysine), poly(4-hydroxy-L-proline ester), poly[α-(4-aminobutyl)-L-glycolic acid], PCL, poly(ortho esterpoly(caprolactone)), PHB, polyethylene imine, polyanhydrides, PHA, PET, NDB, copolymers thereof, and the like. The spacer elements 334 may include a polymer (e.g., a biodegradable or resorbable polymer). For example, the spacer elements 334 may include at least one of PLA, PLGA, PGA, PLLA, PDLA, PDLLA, PLDLLA, poly(L-lactide-co-L-lysine), poly(4-hydroxy-L-proline ester), poly[α-(4-aminobutyl)-L-glycolic acid], PCL, poly(ortho esterpoly(caprolactone)), PHB, polyethylene imine, polyanhydrides, PHA, PET, NDB, copolymers thereof, and the like.

The spacer elements 334 may include a relatively stiff coating or external layer along the length of the elongate member 330. The coating may include a material configured to dissolve relatively quickly, allowing the elongate member 330 to return to a longitudinally shorter shape. The coating may include variable properties along the length of the elongate member 330, for example to allow for timed shape transformation at different stages along the length of the elongate member 330. The timing may, for example, be correlated or matched to the expected or average tissue healing process so as to apply a steady compressive load over the period of healing and strengthening of the tissue. The coating may be variably disposed radially around the elongate member 330, for example to introduce a bending action of the elongate member as the coating dissolves. The bending action may, for example, draw together the wound margins and/or retract the lumen wall to aid healing.

The polymer of the coiled portion 332 and/or the spacer elements 334 may be selected or designed to have a degradation duration greater than an expected or average necrosis duration for a closed inverted diverticulum.

The coiled portion 332 and the spacer elements 334 may include the same polymer or a different polymer. For example, the spacer elements 334 may include a polymer that biodegrades or resorbs more quickly than a polymer of the coiled portion 332. The spacer elements 334 can inhibit or prevent the windings of the coiled portion 332 from contracting such that the coiled portion 332 remains slightly taut. As the polymer of the spacer element 334 biodegrades, the windings of the polymer coiled portion 332 can bunch closer together prior to degrading, as described above.

The coiled portion 332 and/or the spacer elements 334 may include a material that is generally not biodegradable, such as nickel titanium alloy (e.g., nitinol), chromium cobalt alloy, silicone, polytetrafluoroethylene (PTFE), and the like. For example, if the coiled portion 332 includes a metal alloy and the spacer elements 334 include a biodegradable polymer, as the polymer of the spacer element 334 biodegrades, the windings of the coiled portion 332 can bunch closer together, as described above.

The elongate member 330 may be passed or removed with a necrosed diverticulum, or may remain in the body lumen to buttress a known weakened portion of the body lumen.

The elongate members 230, 330 may be relatively simple to manufacture, for example in comparison to a laser-cut closure device or the like. The elongate members 230, 330 may include materials that are currently available and approved for use in the body, which can reduce costs in material development and/or regulatory approval.

Figure 2G:
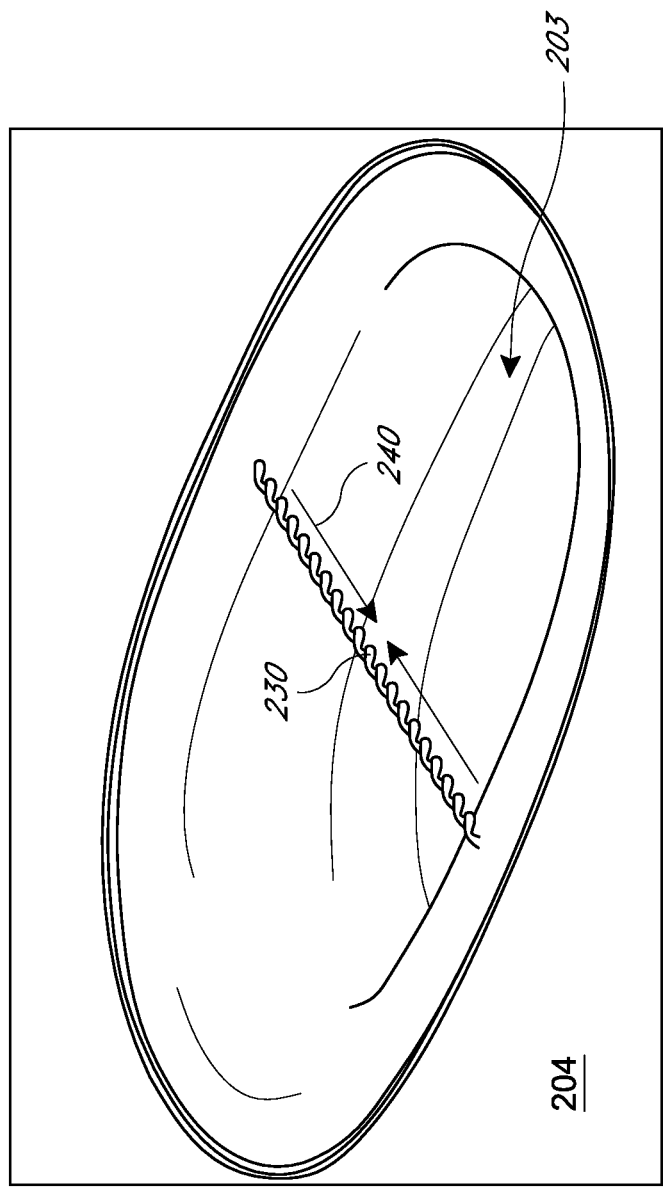

Referring again to FIGS. 2A-2I, FIG. 2F shows the diverticulum 202 after the catheter 220 is retracted from the first region 226 of the muscular layer 206, which removes the elongate member 230 from the lumen of the catheter 220. Upon release from the catheter 220, the windings of the coil can longitudinally contract, as indicated by the arrows 240 at the mouth 203 of the diverticulum 202. The force applied to the tissue is sufficient to assist in bringing the edges together, but is not so great that microvascular blood flow is excluded and tissue health compromised. The force on the tissues may be distributed over as great an area as possible through, for example, coiling, roughening of the surface, and/or the overall length of the elongate member 230. FIG. 2G is a top perspective view of the inverted diverticulum 202, in which the serosa 204 and the mouth 203 are visible, in the same state as FIG. 2F. The elongate member 230, contracting in the direction of the arrows 240, is also visible.

A plurality of catheters 220 including elongate members 230 therein may be stocked or arranged as a cartridge within a deployment system such as a working lumen of a colonoscope. A single catheter 220 may be used to deliver a plurality of elongate members 230, for example the elongate members 230 being stocked or arranged proximal to the catheter 220 within a deployment system such as a working lumen of a colonoscope. Such systems can allow for the substantially parallel or parallel and/or substantially transverse or transverse deployment of the elongate members 230, and more or fewer elongate members 230 can be used in each case as clinically needed. An example device for delivering a plurality of elongate members 230 may include a deployment tube holding a length of elongate material greater than the length of an elongate member 230. The elongate material may be cut after deployment of each elongate member 230. After cutting, a portion of material of the next elongate member 230 can be advanced within the same deployment tube, ready for advancement and cutting. In certain such embodiments, the deployment tube may have an in-and-out action, being moved laterally following each insertion, but broadly being parallel to the previously-inserted elongate member 230. Another example of a device for delivering a plurality of elongate members 230 includes a tubular section that may be retracted from the deployment catheter (e.g., working channel of a colonoscope) after delivering an elongate member 230, reloaded with another elongate member, and then reinserted into the deployment catheter.

FIG. 2H is a top perspective view of the inverted diverticulum 202, in which the serosa 204 and the mouth 203 are visible, after a first plurality of elongate members 230 have been deployed in the same or substantially the same direction as the elongate member 230 described above, for example as described above as being released from a plurality of catheters 220. A second elongate member 230 is disposed in a coiled state through a third region 246 of the muscular layer 206 of the body lumen and through a fourth region 248 of the muscular layer 206 of the body lumen. The inverted diverticulum 202 is between the third region 246 and the fourth region 248. A third elongate member 230 is disposed in a coiled state through a fifth region 256 of the muscular layer 206 of the body lumen and through a sixth region 258 of the muscular layer 206 of the body lumen. The inverted diverticulum 202 is between the third region 256 and the fourth region 258. The disposing can be repeated for each of the plurality of elongate members 230. The device 210 can help to properly space and/or orient the first plurality of elongate members 230, for example by including guide apertures.

The elongate members 230 may be disposed inside-out (e.g., a central elongate member 230 first, then an elongate member proximate to one side of the central elongate member 230, then an elongate member proximate to the other side of the central elongate member 230, and so on). The elongate members 230 may be disposed outside-in (e.g., a first elongate member 230 proximate to a side of the inverted diverticulum 202, then a second elongate member 230 proximate to the other side of the inverted diverticulum 202, then a third elongate member 230 proximate to the first elongate member 230 and between the first elongate member 230 and the second elongate member 230, and so on). Other disposing sequences are also possible.

The first plurality of elongate members 230 are substantially parallel (e.g., having longitudinal axes that do not diverge by more than about 10°) or parallel to each other. The first plurality of elongate members 230 can form a first part of a mesh 234 (FIG. 2I) across the mouth 203 of the inverted diverticulum 202.

The first plurality of elongate members 230 may be the same or substantially the same, or at least some of the first plurality of elongate members 230 may include one or more varying properties. For example, properties that may vary between elongate members 230 include diameter, length, coil pitch, elongate material diameter, radial shape, longitudinal shape, material, surface roughening, coating, spacer elements, drugs, etc.

FIG. 2I is a top perspective view of the inverted diverticulum 202, in which the serosa 204 and the mouth 203 are visible, after a second plurality of elongate members 232 have been deployed in a direction substantially transverse (e.g. crossing at an angle between about 80° and about 100°) or transverse to the elongate members 230 described above, for example as described above as being released from a plurality of catheters 220 or sequentially from a single catheter. The second plurality of elongate members 232 are substantially parallel (e.g., having longitudinal axes that do not diverge by more than about 10°) or parallel to each other. The device 210 can help to properly space and/or orient the second plurality of elongate members 232, for example by including guide apertures and/or spacing indicators.

If the second elongate members 232 are disposed after the first elongate member 230 (e.g., after the state illustrated in FIG. 2G), a second elongate member 232 is disposed in a coiled state through a third region 266 of the muscular layer 206 of the body lumen and through a fourth region 268 of the muscular layer 206 of the body lumen. The inverted diverticulum 202 is between the third region 266 and the fourth region 268. A third elongate member 230 is disposed in a coiled state through a fifth region 276 of the muscular layer 206 of the body lumen and through a sixth region 278 of the muscular layer 206 of the body lumen. The inverted diverticulum 202 is between the third region 276 and the fourth region 278. The disposing can be repeated for each of the plurality of elongate members 232.

The second plurality of elongate members 232 may be the same or substantially the same, or at least some of the second plurality of elongate members 232 may include one or more varying properties. For example, properties that may vary between elongate members 232 include diameter, length, coil pitch, elongate material diameter, radial shape, longitudinal shape, material, surface roughening, coating, spacer elements, drugs, etc.

The first plurality of elongate members 230 and the second plurality of elongate members 232 may be disposed sequentially (e.g., as illustrated in FIGS. 2H and 2I). The first plurality of elongate members 230 and the second plurality of elongate members 232 may be disposed intermittently, for example alternating between disposing an elongate member 230 and disposing an elongate member 232. Other sequences of disposing the first plurality of elongate members 230 and the second plurality of elongate members 232 are also possible.

The second plurality of elongate members 232 can form a second part of a mesh 234 across the mouth 203 of the inverted diverticulum 202. The pluralities of elongate members 230, 232 together create a mesh 234 across the mouth 203 of the inverted diverticulum 202. The elongate members 230, 232 may include a non-coiled or flattened portion proximate to at least one expected crossing point with other elongate members 230, 232, for example to inhibit constriction due to coil interaction at the crossing point.

The first plurality of elongate members 230 and the second plurality of elongate members 232 may be the same or substantially the same, or at least some of the first plurality of elongate members 230 may include one or more varying properties versus at least some of the second plurality of elongate members 232. For example, properties that may vary between elongate members 230, 232 include diameter, length, coil pitch, elongate material diameter, radial shape, longitudinal shape, material, surface roughening, coating, spacer elements, drugs, etc.

The cross pinning of the smooth muscle tissue allows and can guide tissue migration across the mouth 203, initially by fibrocytes and then by smooth muscle cells. The longitudinal and transverse placement of the elongate members 230, 232 can match the orientation of the two muscle layers of the bowel wall.

The two layers of the elongate members 230, 232 can allow for a timed healing process. Swelling due to agitation of the area is accounted for as well as the need for increased security of the seal over time. This "smart" technology is not present in current suturing methods and devices. In some embodiments, multiple types of elongate members 230, 232, for example a first "healing" type and a second "securing" type, may be alternately deployed, with the former acting as a tissue guide or bridge and the latter acting to draw the tissue edges together. In certain such embodiments, the "healing" type elongate members may be aligned with the muscle fibers and the "securing" type elongate members may be aligned normal to the fibers at each layer.

The combination of the coiling to close the gap 203 of the inverted diverticulum 202, the tissue growth stimulating nature of the mesh 234 of darts 230, 232, and the inversion of the diverticulum 202 itself, for example acting as a flap valve, can promote long term closure of the wall of the body lumen. By contrast, a suture or the like that attempts to close the mouth of an inverted diverticulum at the time of treatment may be difficult to employ and may be ineffective due to inflammation or irritation of the tissue during the treatment. The tissue of the inverted diverticulum 202 can shrink, necrose, and/or slough off in situ, for example because pressure is inward from the lumen of the colon rather than outward.

Figure 5:
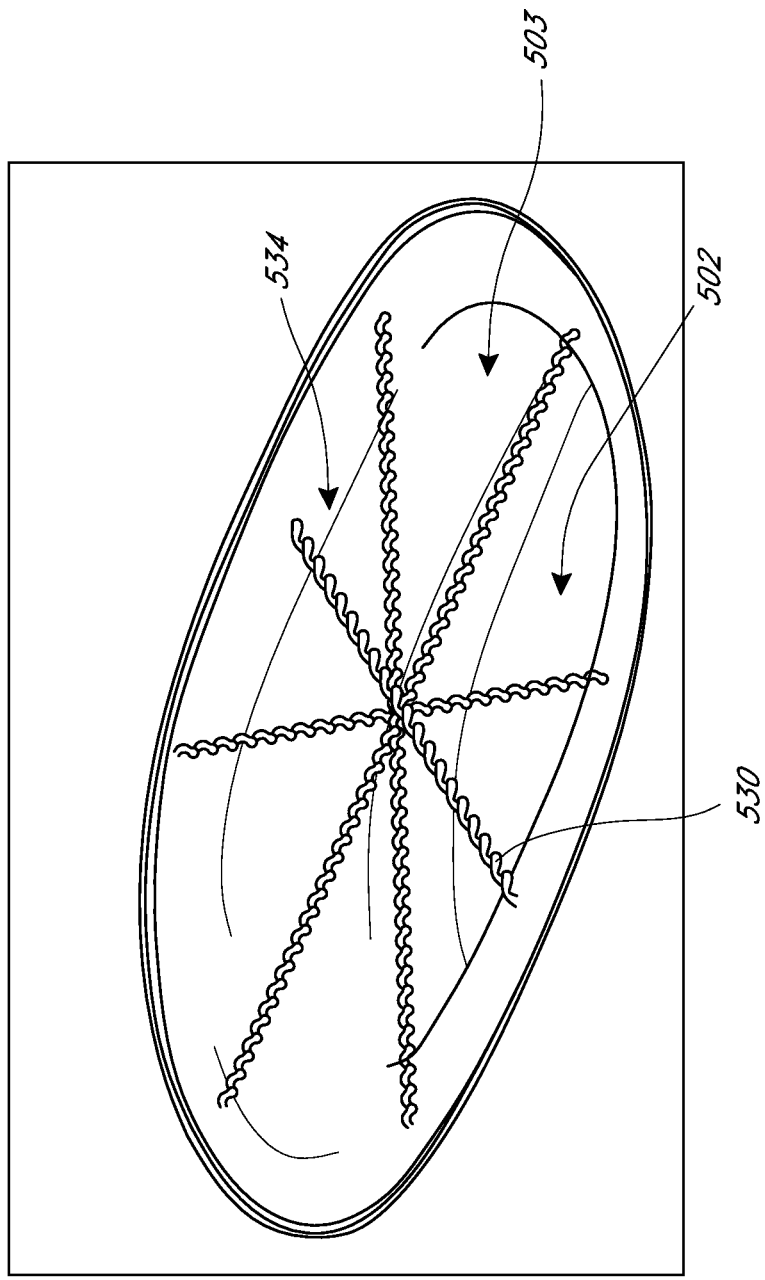
FIG. 5 is a top perspective view of another example of a treated diverticulum.

FIG. 5 is a top perspective view of another example of a treated diverticulum 504. A plurality of elongate members 530, which may be for example similar to the elongate members 230, 330 described above, form a star or asterisk pattern across the mouth 203 of the inverted diverticulum 502. This pattern can help to retract the mouth 203 toward a central point. The thickness of the elongate members 530 at a central crossing point may be large, so it may be desirable to slightly offset the elongate members 530 around a central crossing point. The device 210 described above can help to orient the elongate members 530. The elongate members 530 create a mesh 534 across the mouth 503 of the inverted diverticulum 502. The elongate members 530 may include a non-coiled or flattened portion proximate to the expected crossing point of the elongate members 530, for example to inhibit constriction due to coil interaction at the crossing point.

While the description generally refers to colonoscopes and treatments within a colon, the devices and methods described herein are not limited to applications within a colon. They can be used to invert and/or treat outpocketings (e.g., diverticula, aneurysms, etc.) in any body lumen. Any reference to a colonoscope should be understood to be applicable to endoscopes generally, and similarly, any reference to a colon should be understood to be applicable to any body lumen.

A contractile mesh may also be used for applications without a lumen and/or without an outpocketing. For example, the devices and methods described above may be useful for moving fascial planes in a given direction, such as for a face lift procedure. The elongate members could be placed along the desired line(s) of lift, divergent and/or parallel, and the variable resorption rate can be used to define a period of the lift action. Such a procedure may be used to reduce or remove wrinkles. The lift action can be applied over time, with each application of elongate members adding to and modulating the effects of prior applications. Such procedures can reduce or remove the surgical risk of not achieving an appropriate balance and/or scarring and healing not being according to plan, for example because the process may be performed gradually and potentially without the need for surgical intervention. For another example, the devices and methods described above may be useful for reinforcing the Coopers Ligaments of the breast to reverse the progressive and natural sagging of breast tissue over time. A progressive approach in which additional elongate members may be added is feasible. For yet another example, the device and methods described herein may be applied to pelvic floor, abdominal herniation, and sphincter reinforcement, keeping the same principle of a supple and springy compound to obtain desired tissue tensions while applying appropriate force to the tissues to rectify the particular complaint (e.g., prolapse, herniation, incontinence, etc.). For such implementations, the elongate members may have more robust dimensions than described above (e.g., thicker elongate material, larger diameter, larger length, different material, etc.).

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

EXAMPLE EMBODIMENTS

The following example embodiments identify some possible permutations of combinations of features disclosed herein, although other permutations of combinations of features are also possible.

1. A method for treating a diverticulum in a body lumen, the method including:
   disposing an elongate member in a coiled state through a first region of a muscular layer of the body lumen and through a second region of the muscular layer of the body lumen, the diverticulum being inverted and between the first region and the second region.

2. The method of Embodiment 1, wherein disposing the elongate member includes:
   inserting a tubular member through the first region of the muscular layer and through the second region of the muscular layer, wherein, during inserting the tubular member, the elongate member is in an extended state in a lumen of the tubular member; and
   removing the elongate member from the lumen of the tubular member.

3. The method of Embodiment 2, further including disposing a collar around a mouth of the inverted diverticulum.

4. The method of any one of Embodiments 1-3, wherein the elongate member in the coiled state includes a coiled portion and one or more spacer elements between windings of the coiled portion, wherein the spacer elements are longitudinally compressible by the coiled portions.

5. The method of any one of Embodiments 1-4, further including disposing a second elongate member in a coiled state through a third region of the muscular layer of the body lumen and through a fourth region of the muscular layer of the body lumen, the inverted diverticulum between the third region and the fourth region.

6. The method of Embodiment 5, wherein after disposing the elongate member and disposing the second elongate member, a longitudinal axis of the elongate member and a longitudinal axis of the second elongate member form an angle that is less than about 10°.

7. The method of Embodiment 5, wherein after disposing the elongate member and disposing the second elongate member, a longitudinal axis of the elongate member and a longitudinal axis of the second elongate member form an angle that is between about 80° and about 100°.

8. The method of any one of Embodiments 5-7, wherein disposing the second elongate member includes:
inserting a second tubular member through the third region of the muscular layer and through the fourth region of the muscular layer, wherein, during inserting the second tubular member, the second elongate member is in an extended state in a lumen of the second tubular member; and
removing the second elongate member from the lumen of the second tubular member.

9. The method of any one of Embodiments 1-8, further including disposing a plurality of elongate members through regions of the muscular layer of the body lumen on opposite sides of the inverted diverticulum.

10. The method of Embodiment 9, wherein the plurality of elongate members includes a first plurality of elongate members substantially parallel to each other and a second plurality of elongate members substantially parallel to each other and substantially transverse to the first plurality of elongate members.

11. The method of any one of Embodiments 1-10, further including, prior to disposing the elongate member, inverting the diverticulum.

12. The method of any one of Embodiments 1-10, wherein the body lumen includes an intestine.

13. The method of any one of Embodiments 1-12, wherein the elongate member is not a guide wire.

14. A system for treating a diverticulum in a body lumen, the system including:
a tubular member including a lumen; and
an elongate member in an elongated state within the lumen of the tubular member, the elongate member configured to form a coiled state when removed from the tubular member.

15. The system of Embodiment 14, further including a pusher configured to maintain a longitudinal position of the elongate member upon retraction of the tubular member.

16. The system of Embodiment 14 or 15, wherein the elongate member is bioabsorbable.

17. The system of any one of Embodiments 14-16, wherein the elongate member includes a polymer.

18. The system of Embodiment 17, wherein the polymer includes at least one of polylactic acid (PLA), poly(lactic-co-glycolic acid) (PLGA), polyglycolic acid (PGA), poly-L-lactic acid (PLLA), poly-D-lactic acid (PDLA), poly-D,L-lactic acid (PDLLA), poly(L-lactic-co-D,L-lactic acid) (PLDLLA), poly(L-lactide-co-L-lysine), poly(4-hydroxy-L-proline ester), poly[α-(4-aminobutyl)-L-glycolic acid], polycaprolactone (PCL), poly(ortho esterpoly(caprolactone)), polyhydroxybutyrate (PHB), polyethylene imine, polyanhydrides, polyhydroxyalkanoate (PHA), polyethylene terephthalate (PET), naturally derived bioabsorbable polymers (NDB), and copolymers thereof.

19. The system of any one of Embodiments 14-18, wherein the elongate member in the coiled state has a length of less than about 5 cm.

20. The system of any one of Embodiments 14-19, wherein the elongate member in the coiled state has a radius of less than about 1 mm.

21. The system of any one of Embodiments 14-20, wherein the elongate member in the coiled state has a pitch of less than about 1 mm.

22. The system of any one of Embodiments 14-21, wherein the elongate member includes a textured surface.

23. The system of any one of Embodiments 14-22, wherein the elongate member includes a coiled portion and one or more spacer elements between windings of the coiled portion, wherein the spacer elements are longitudinally compressible by the coiled portions.

24. The system of Embodiment 23, wherein the coiled portion is bioabsorbable, the spacer elements are bioabsorbable, and the spacer elements are configured to have a rate of bioabsorbtion that is greater than a rate of bioabsorbtion for the coiled portion.

25. The system of any one of Embodiments 14-24, wherein the elongate member is not a guide wire.

26. An assembly for treating a diverticulum in a body lumen, the assembly including:
a catheter including a working channel; and
the system of any one of Embodiments 14-25 at least partially within the working channel.

27. The assembly of Embodiment 26, wherein a colonoscope includes the catheter, the colonoscope further including a light source and a viewing lens.

28. An assembly for treating a diverticulum in a body lumen, the assembly including:
a catheter including a working channel; and
a plurality of the system of any one of Embodiments 14-25 at least partially within the working channel.

29. The assembly of Embodiment 28, wherein a colonoscope includes the catheter, the colonoscope further including a light source and a viewing lens.

What is claimed is:

1. A method to treat a diverticulum in a body lumen, the method comprising:
disposing an elongate member in a coiled state through a first region of a muscular layer of the body lumen and through a second region of the muscular layer of the body lumen, the diverticulum being inverted and between the first region and the second region, wherein the elongate member in the coiled state comprises a coiled portion and a plurality of spacer elements, wherein the plurality of spacer elements are longitudinally compressible by the coiled portion, wherein the plurality of spacer elements have a higher rate of biosorption than the coiled portion of the elongate member, and wherein each plurality of spacer elements that include a biodegradable polymer is positioned between windings of the coiled portion such that the windings of the coiled portion are stretched apart, and wherein degradation of the biodegradable polymer leads to contraction of the windings of the coiled portion.

2. The method of claim 1, wherein disposing the elongate member comprises:
inserting a tubular member through the first region of the muscular layer and through the second region of the muscular layer, wherein, during inserting the tubular member, the elongate member is in an extended state in a lumen of the tubular member; and
removing the elongate member from the lumen of the tubular member.

3. The method of claim 2, further comprising disposing a collar around a mouth of the inverted diverticulum.

4. The method of claim 1, further comprising disposing a second elongate member in a coiled state through a third region of the muscular layer of the body lumen and through a fourth region of the muscular layer of the body lumen, the inverted diverticulum between the third region and the fourth region.

5. The method of claim 4, wherein after disposing the elongate member and disposing the second elongate member, a longitudinal axis of the elongate member and a longitudinal axis of the second elongate member form an angle that is less than about 10°.

6. The method of claim 4, wherein after disposing the elongate member and disposing the second elongate member, a longitudinal axis of the elongate member and a longitudinal axis of the second elongate member form an angle that is between about 80° and about 100°.

7. The method of claim 4, wherein disposing the second elongate member comprises:
inserting a second tubular member through the third region of the muscular layer of the body lumen and through the fourth region of the muscular layer of the body lumen, wherein, during inserting the second tubular member, the second elongate member is in an extended state in a lumen of the second tubular member; and
removing the second elongate member from the lumen of the second tubular member.

8. The method of claim 1, further comprising disposing a plurality of elongate members through regions of the muscular layer of the body lumen on opposite sides of the inverted diverticulum.

9. The method of claim 8, wherein the plurality of elongate members comprises a first plurality of elongate members substantially parallel to each other and a second plurality of elongate members substantially parallel to each other and substantially transverse to the first plurality of elongate members.

10. The method of claim 1, further comprising, prior to disposing the elongate member, inverting the diverticulum.

11. The method of claim 1, wherein the body lumen comprises an intestine.

12. The method of claim 1, wherein the elongate member is not a guide wire.

13. The method of claim 1, wherein a spacer element of the plurality of spacer elements are absent from ends of the elongate member.

14. The method of claim 1, wherein the biodegradable polymer comprises at least one of polylactic acid (PLA), poly(lactic-co-glycolic acid) (PLGA), polyglycolic acid (PGA), poly-L-lactic acid (PLLA), poly-D-lactic acid (PDLA), poly-D,L-lactic acid (PDLLA), poly(L-lactic-co-D,L-lactic acid) (PLDLLA), poly(L-lactide-co-L-lysine), poly(4-hydroxy-L-proline ester), poly[a-(4-aminobutyl)-L-glycolic acid], polycaprolactone (PCL), poly(ortho esterpoly (caprolactone)), polyhydroxybutyrate (PHB), polyethylene imine, polyanhydrides, polyhydroxyalkanoate (PHA), polyethylene terephthalate (PET), naturally derived bioabsorbable polymers (NDB), and copolymers thereof.

* * * * *

UNITED STATES PATENT AND TRADEMARK OFFICE
CERTIFICATE OF CORRECTION

PATENT NO. : 9,877,727 B2  
APPLICATION NO. : 14/001764  
DATED : January 30, 2018  
INVENTOR(S) : Ozdil et al.

Page 1 of 1

It is certified that error appears in the above-identified patent and that said Letters Patent is hereby corrected as shown below:

In Column 1, Line 4, delete "APPLICATIONS" and insert -- APPLICATION --, therefor.

In Column 1, Line 7, delete "PCT" and insert -- International --, therefor.

In Column 1, Line 10, delete "in their" and insert -- in its --, therefor.

In Column 5, Line 10, delete "colon 102)." and insert -- colon 100). --, therefor.

In Column 5, Line 14, delete "colon 102." and insert -- colon 100. --, therefor.

In Column 5, Line 40, delete "an diverticulum" and insert -- the diverticulum --, therefor.

In Column 5, Line 66, delete "mucosal layer 206" and insert -- mucosal layer 208 --, therefor.

In Column 6, Line 19, delete "second side 228" and insert -- second region 228 --, therefor.

In Column 6, Line 22, delete "muscle layer 206" and insert -- muscular layer 206 --, therefor.

In Column 6, Line 24, delete "muscle layer 206" and insert -- muscular layer 206 --, therefor.

In Column 11, Line 2, delete "(e.g." and insert -- (e.g., --, therefor.

In Column 13, Line 36, delete "recitation no" and insert -- recitation, no --, therefor.

In Column 13, Line 58, delete "general such" and insert -- general, such --, therefor.

In Column 13, Line 65, delete "general such" and insert -- general, such --, therefor.

In Column 16, Line 61, in Claim 1, delete "each plurality" and insert -- each of the plurality --, therefor.

Signed and Sealed this  
Seventeenth Day of April, 2018

Andrei Iancu  
*Director of the United States Patent and Trademark Office*